United States Patent [19]

Tucker et al.

[11] 4,248,594
[45] Feb. 3, 1981

[54] NICKEL SALT-ESTER STABILIZING COMPOSITIONS

[75] Inventors: Robert J. Tucker, Hackettstown; Joseph A. Hoffman, Bridgewater, both of N.J.

[73] Assignee: American Cyanamid Company, Stamford, Conn.

[21] Appl. No.: 118,256

[22] Filed: Feb. 4, 1980

[51] Int. Cl.$^3$ .................. C09B 45/00; D06P 1/10
[52] U.S. Cl. ................................. 8/583; 8/DIG. 9; 252/8.6; 260/45.75 N; 260/439 R; 8/928; 8/594
[58] Field of Search ............ 8/180, 92, DIG. 9, 42 D; 260/45.75 N, 439 R

[56] References Cited

U.S. PATENT DOCUMENTS

| | | | |
|---|---|---|---|
| 3,189,630 | 6/1965 | Smutny | 260/45.75 N |
| 4,144,029 | 3/1979 | Hoffman et al. | 260/45.75 N |

OTHER PUBLICATIONS

"Coloration of Propylene", P. N. Hartley, International Dyer, 1965, vol. 134, pp. 541–543.

*Primary Examiner*—A. Lionel Clingman
*Attorney, Agent, or Firm*—Bruce F. Jacobs

[57] ABSTRACT

Compositions of nickel salts of 4-hydroxybenzoic acids and esters of aliphatic or aromatic carboxylic acids, which esters have boiling points of at least about 250° C. are useful for stabilizing polyolefins against degradation by heat and ultraviolet radiation and for rendering polyolefins dyeable.

20 Claims, No Drawings

NICKEL SALT-ESTER STABILIZING COMPOSITIONS

This invention relates to nickel salt-ester compositions useful for stabilizing polyolefins against degradation by ultraviolet light. More particularly, it relates to said stabilization of polyolefin multifilament fibers, particularly polypropylene multifilament fibers, by the use of (a) a nickel salt light stabilizer and dye enhancer represented by formula (I):

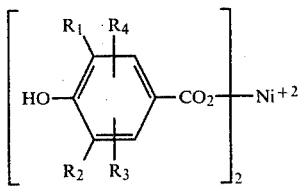

wherein $R_1$ and $R_2$ are each alkyl radicals containing up to 8 carbon atoms, at least one of which is branched on the alpha carbon atom, and $R_3$ and $R_4$ are each hydrogen or an alkyl radical containing up to 18 carbon atoms, and (b) an aliphatic or aromatic ester of a carboxylic acid.

Polyolefins, particularly polypropylene, are important as textile fibers because of the economic and physical advantages they offer. However, the poor dyeability of such fibers has been a problem. One method of improving the dyeability of these materials has been to blend the polyolefin with a nickel compound which can serve as a dyesite for chelatable dyes.

Nickel compounds, represented by formula (I), are known to be excellent stabilizers to prevent degradation by ultraviolet radiation and to provide suitable dyesites for chelatable dyes. However, when these compounds are dry blended with a polyolefin and processed at high temperatures (290° C.), they decompose and produce gaseous bubbles in the resulting polyolefin composition. Because of the thermal instability of these compounds, they have not been widely used as ultraviolet stabilizers.

Hoffman et al., U.S. Pat. No. 4,144,029, the disclosure of which is incorporated herein by reference, provides a nickel stabilizer composition which is effective in stabilizing polyolefins against degradation caused by light, and also in enhancing the dyeability of polypropylene with chelatable dyes, preferably water-dispersible aromatic monoazo dyes having a hydroxyl group at one position ortho to the azo group. The composition comprises the reaction product of (a) 30-90 parts by weight of a compound represented by formula (I), and (b) 70-10 parts by weight of a secondary or tertiary organic phosphite.

However, the compositions of Hoffman et al. have deficiencies in that the phosphite has been found to sublime out during processing in the polyolefin, and form an insoluble residue which may clog the spinnerette holes. These deficiencies are overcome by the present invention.

In accordance with the present invention, there is provided a method for rendering a polyolefin resistant to ultraviolet degradation by incorporating into said polyolefin about 0.05% by weight to about 10% by weight, preferably from about 0.25% by weight to about 2% by weight, based on the weight of said polyolefin, of a mixture of about 70 to 90% by weight of a compound of formula (I) and about 30 to 10% by weight of an aliphatic or aromatic ester of a carboxylic acid.

In the preferred embodiment, the polyolefin is polypropylene, the compound of formula (I) is nickel 3,5-di-tert.-butyl-4-hydroxybenzoate, and the ester is dibutyl phthalate.

The invention also pertains to the compositions obtained by the method described above and a method for dyeing the compositions obtained by treating the same with a chelating aromatic hydroxy azo dye.

The nickel salts of the following acids are illustrative of the compounds of formula (I):
3,5-di-tert.-butyl-4-hydroxybenzoic acid.
3,5-diisopropyl-4-hydroxybenzoic acid,
3,5-di-sec.-butyl-4-hydroxybenzoic acid,
3-isopropyl-5-tert.-butyl-4-hydroxybenzoic acid,
3,5-di-cyclohexyl-4-hydroxybenzoic acid,
3-methyl-5-tert.-butyl-4-hydroxybenzoic acid,
2,6-dimethyl-3,5-di-tert.-butyl-4-hydroxy enzoic acid.
2-nonyl-3,5-di-tert.-butyl-4-hydroxybenzoic acid,
3,5-di-tert.-amyl-4-hydroxybenzoic acid,
3,5-di-tert.-octyl-4-hydroxybenzoic acid, and the like.

These salts can be prepared by stirring a dilute solution of the corresponding sodium salt with an aqueous solution containing an equivalent amount of nickel chloride and recovering the precipitated nickel salt by conventional methods.

The above mentioned sodium salt can be prepared by methods disclosed by Smutny in U.S. Pat. No. 3,189,630, e.g. Example I.

The preparation of the preferred compound of formula (I), nickel 3,5-di-tert.-butyl-4-hydroxybenzoate, is disclosed in Example 1 of U.S. Pat. No. 4,144,029.

The esters useful in the present invention are those esters of aliphatic carboxylic acids and aromatic carboxylic acids which esters have a boiling point of at least about 250° C. The following are illustrative of the esters which may be used in this invention:
n-hexadecyl 3,5-di-tert.-butyl-4-hydroxybenzoate,
di-n-butyl phthalate,
di-n-octyl phthalate
di-2-ethylhexyl phthalate
2-tert.-butyl-4-methylphenyl benzoate,
n-octadecyl 4-hydroxybenzoate,
1,2-ethanediyl distearate,
octadecyl 3-(3,5-di-tert.-butyl-4-hydroxyphenyl)propionate,
pentaerythrityl tetrakis-3-(3,5-di-tert.-butyl-4-hydroxyphenyl)propionate,
and the like, including polymeric esters of polyglycols such as:
poly(ethylene terephthalate),
poly(ethylene adipate),
poly(ethylene succinate),
poly(1,4-cyclohexanedimethylene terephthalate),
poly(1,4-cyclohexanedimethylene succinate), and the like.

Also useful are esters of polyetherglycols. Suitable such compounds include those of the formula

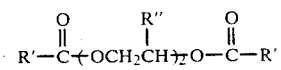

wherein R' is alkyl ($C_{1-17}$) or aryl, R" is hydrogen or alkyl ($C_{1-4}$), and n is an integer of at least two. These include:

diethylene glycol diacetate,
diethylene glycol dibenzoate,
diethylene glycol distearate,
di-(2-methylethylene) glycol diacetate, and the like.

The preferred ester is di-butyl phthalate.

As used herein, the term "polyolefin" includes homopolymers of alpha olefins such as polyethylene, polypropylene, polystyrene, polybutadiene, polybutylene, polyisoprene, and the like, and copolymers such as ethylenepropylene copolymer, ethylenebutylene copolymer, ethylenevinyl acetate copolymer, styrenebutadiene copolymer, acrylonitrile-styrene-butadiene copolymer, and the like. The preferred polyolefin is polypropylene.

The stabilizers of this invention may be incorporated into polyolefins by any of the various procedures known in the art such as by dry blending the compositions with the polyolefin in powder or granular form, followed by milling, Banbury mixing, molding, casting, extruding, swelling, and the like, to obtain a polyolefin fiber, film, fabric, molded article, or thermoformed article.

The amounts of the composition needed to be effective will depend on the effect sought and on the particular composition used.

The thermal stability of the polyolefin composition is determined by cutting the material into strips; inserting the strips in a Melt Index Apparatus (ASTM D1238) at 290° C.; and extruding the material after a residence period of 5 or 10 minutes. The extrudate is then inspected for gassing, as evidenced by the presence of bubbles.

The compositions of the invention were also evaluated by dry blending with the polypropylene and melt spinning through a 30-hole (0.020" d. ×0.040") spinnerette under the following conditions:

| Filter Pack | | Bound Screens 80-200 mesh |
|---|---|---|
| Temperatures - | Spin Pack | 500° F. |
| | Pump Block | 490° F. |
| | Smear Head | 485° F. |
| | Barrel Forward | 450° F. |
| | Barrel Rear | 390° F. |
| | Column Top | 225° F. avg. |
| Pack Pressure | Group 1 | 350-400 psig |
| | Group 2 | 250-300 psig |
| Output | | 1.2 lb/hr |
| Shear Rate | | 65 sec$^{-1}$ |
| Spin Draw | | 100;1 |

The multifilaments were then drawn under the following conditions:

| Stage 1 | |
|---|---|
| Temperature | 220° F. |
| Ratio | 5:1 |
| Stage 2 | |
| Temperature | 280° F. |
| Ratio | 1.2:1 |
| Draw (overall) | 6:1 |

The use of the compositions of this invention is not limited to the above conditions, which are described for the purpose of illustration only.

The chelatable dyes, which are useful for dyeing or printing polyolefins containing the compositions of this invention, include aromatic ortho hydroxy azo dyes, such as aromatic ortho hydroxy mono-azo and conjugated di- and multi- azo dyes. These include the polypropylene series of dyes which are disclosed in U.S. Pat. No. 4,144,029.

In the following non-limiting examples all parts and percents are by weight unless otherwise specified.

EXAMPLE 1

Unstabilized polypropylene (100 parts) is dry-blended with 0.2 part of a primary-type phenolic-phosphite antioxidant (CYANOX® 1735 Antioxidant; American Cyanamid Company), 0.1 part of calcium stearate, 0.7 part of nickel 3,5-di-tert.-butyl-4-hydroxybenzoate, and 0.3 part of n-hexadecyl 3,5-di-tert.-butyl-4-hydroxybenzoate. The blended mixture is milled on a standard two-roll mill at about 190° C. cut into strips, and inserted into a Melt Index Apparatus at 290° C. After aging at 290° C. for 5 minutes, an extrudate is removed from the apparatus and inspected for thermal decomposition as evidenced by the presence of bubbles. No bubbles were observed.

When the experiment was repeated without the n-hexadecyl 3,5-di-tert.-butyl-4-hydroxybenzoate, the extrudate contained bubbles.

EXAMPLES 2–9

Example 1 was repeated except that 0.3 part by weight of the esters shown below were substituted for the n-hexadecyl 3,5-di-tert.-butyl-4-hydroxybenzoate. In all cases, no evidence of bubbling was found.

| Example | Ester Utilized |
|---|---|
| 2 | phenyl-1,2-di(C(=O)-O-C$_4$H$_9$) (dibutyl phthalate) |
| 3 | phenyl-1,2-di(C(=O)-O-C$_8$H$_{17}$) |
| 4 | phenyl-C(=O)-O-[2-(CH$_3$)$_3$C, 4-CH$_3$ phenyl] |
| 5 | HO-phenyl-C(=O)-O-C$_{18}$H$_{37}$ |
| 6 | C[-CH$_2$-O-C(=O)-CH$_2$CH$_2$-(3,5-di-C(CH$_3$)$_3$-4-OH-phenyl)]$_4$ |
| 7 | 3,5-di-(CH$_3$)$_3$C-4-HO-phenyl-CH$_2$CH$_2$-C(=O)-O-C$_{18}$H$_{37}$ |
| 8 | C$_{17}$H$_{35}$-C(=O)-O CH$_2$CH$_2$O-C(=O)-C$_{17}$H$_{35}$ |
| 9 | phenyl-C(=O)-O C$_{18}$H$_{37}$ |

EXAMPLE 10

A dry blend of stabilized polypropylene powder (100 parts), containing 0.05 part 2,6-di-tert.-butyl-4-methylphenol, 0.05 part octadecyl 3,5-di-tert.-butyl-4-hydroxycinnamate, 0.1 part calcium stearate, 0.7 part of nickel 3,5-di-tert.-butyl-4-hydroxybenzoate, and 0.3 part of dibutyl phthalate was prepared, extruded at 225° C., and pelletized. The pellets were then spun and drawn into multifilaments of 8-9 deniers per fiber using the spinning and drawing conditions previously described. There was no evidence of bubbling, or the presence of an exudate, in the spun yarns. The fibers had acceptable tensile strength and tenacity.

EXAMPLE 11

Example 10 was repeated substituting 0.3 part of n-hexadecyl 3,5-di-tert.-butyl-4-hydroxybenzoate for the dibutyl phthalate. There was no evidence of bubbling, or exudate, in the spun yarn. The spun and drawn yarn showed acceptable dyeability.

Evaluation of the light stability of the multifilaments in a xenon are Atlas Weather-Ometer ® (Atlas Electric Devices Company, Chicago, Ill.) showed that 2000 hours were required to reach a loss of 50% in the breaking strength, versus 980 hours for multifilaments containing 1% by weight of [2,2'-thiobis(4-tert.-octylphenolato)]n-butylamine nickel (II), a well-known ultraviolet light stabilizer represented by the formula

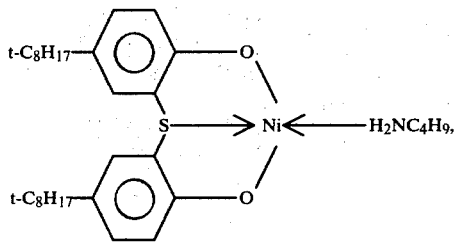

and 100 hours for multifilaments containing no stabilizer.

EXAMPLE 12

The dyeability of various polyolefin compositions was determined by compression molding the extrudate into thin films (4-5 mils) after blending, milling and aging 5 minutes at 290° C., as described in Example 1. Each film contained 0.7% by weight of nickel 3,5-di-tert.-butyl-4-hydroxybenzoate and 0.3% by weight of an ester. The films were then cleaned by immersion in an aqueous solution (60° C.) containing 0.5% by weight of isoctyl phenoxy polyethyoxy ethanol and rinsed with water. The cleansed films were then immersed for 10 minutes in separate aqueous dye baths (95°-100° C.) containing 0.13% by weight of Polypropylene Green BM or Polypropylene Scarlet RBM; each dye bath also contained 2% by weight of citric acid and 0.1% by weight of a nonylphenol ethylene oxide polymer (DECERESOL ® Surfactant NI; American Cyanamid Company). The dyeability was then qualitatively assessed by visual inspection of the dyed films relative to films containing 1% [2,2'-thiobis(4-tert.-octylphenolato)]n-butylamine nickel (II) (CYASORB ® UV 1084 light absorber; American Cyanamid Company), a known chelatable dyesite. The results obtained are shown in Table I.

TABLE I

| Ester Used | Dyeability With | |
|---|---|---|
| | Scarlet RBM | Green BM |
| A | Excellent | Excellent |
| B | " | " |
| C | " | " |
| D | " | Very Good |
| E | " | Very Good |
| F | " | Good |
| G | " | " |
| H | " | " |

A = n-octadecyl p-hydroxybenzoate
B = 2-tert.-butyl-4-methylphenyl benzoate
C = n-octadecyl benzoate
D = n-hexadecyl 3,5-di-tert.-butyl-4-hydroxybenzoate
E = pentaerythrityl tetrakis-3-(3,5-di-tert.-butyl-4-hydroxyphenyl)propionate
F = di-butyl phthalate
G = n-octadecyl 3-(3,5-di-tert.-butyl-4-hydroxyphenyl)propionate
H = 1,2-ethanediyl distearate

EXAMPLES 13-15

The procedure of Example 1 was repeated except using esters which boil below about 250° C. The esters used, their boiling points, and the results were:

| Example | Ester | Boiling Point | Results |
|---|---|---|---|
| 13 | $CH_2(CO_2C_2H_5)_2$ | 200° C. | Bubbling |
| 14 | 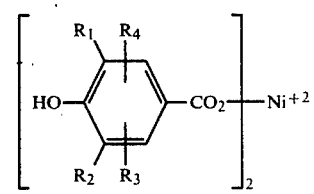 | 212° C. | Bubbling |
| 15 | | 249° C. | V. Slight Bubbling |

What is claimed is:

1. A nickel stabilizer composition for rendering polyolefins dyeable and resistant to degradation by heat and ultraviolet radiation comprising a mixture of about 70 to 90 parts by weight of a compound of formula (I)

$$\left[ HO \underset{R_2 \ R_3}{\overset{R_1 \ R_4}{\bigcirc}} CO_2 \right]_2 Ni^{+2} \quad (I)$$

wherein $R_1$ and $R_2$ are each alkyl radicals having up to 8 carbon atoms at least one of which is branched on the alpha carbon, and $R_3$ and $R_4$ are each hydrogen or an alkyl radical having up to 18 carbon atoms, and about 30 to 10 parts by weight of an ester of an aliphatic or aromatic carboxylic acid, which ester has a boiling point of at least about 250° C.

2. A composition of claim 1 wherein the compound of formula I is nickel 3,5-di-t-butyl-4-hydroxybenzoate.

3. A composition of claim 1 or 2 wherein the ester is di-butyl phthalate.

4. A composition of claim 1 or 2 wherein the ester is n-hexadecyl 3,5-di-t-butyl-4-hydroxybenzoate.

5. A dyeable and heat and ultraviolet radiation resistant composition comprising a polyolefin and from about 0.05 to 10% by weight of the composition of claim 1, based on the weight of the polyolefin.

6. A composition of claim 5 containing about 0.25 to 2% by weight of the composition of claim 1, based on the weight of the polyolefin.

7. A composition of claim 6 wherein the polyolefin is polypropylene.

8. A composition of claim 7 wherein the ester is di-butyl phthalate or n-hexadecyl 3,5-di-t-butyl-4-hydroxybenzoate.

9. A method for dyeing, or printing, a polyolefin fiber, film, or fabric comprising the steps of:
(a) incorporating into said polyolefin from about 0.05% to about 10% by weight of a mixture of about 70 to 90 parts by weight of a compound of formula (I)

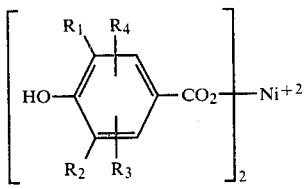

(I)

wherein $R_1$ and $R_2$ are each alkyl radicals having up to 8 carbon atoms at least one of which is branched on the alpha carbon, and $R_3$ and $R_4$ are each hydrogen or an alkyl radical having up to 18 carbon atoms, and about 30 to 10 parts by weight of an ester of an aliphatic or aromatic carboxylic acid, which ester has a boiling point of at least about 250° C., based on the weight of the polyolefin;
(b) forming fibers, films, or fabrics therefrom; and
(c) contacting said fibers, films, or fabrics with a chelatable dye.

10. The method of claim 9 wherein the effective amount of said mixture of formula (I) and ester is from about 0.25% to about 2%, based on the weight of said polyolefin.

11. The method of claim 9 wherein the polyolefin is polypropylene.

12. The method of claim 9 wherein the compound of formula (I) is nickel 3,5-di-tert.-butyl-4-hydroxybenzoate.

13. The method of claim 12 wherein the ester is dibutyl phthalate.

14. The method of claim 12 wherein the ester is n-hexadecyl 3,5-di-tert.-butyl-4-hydroxy-benzoate.

15. The method of claim 9 wherein the dye is an aromatic hydroxy azo dye.

16. The dyed composition of claim 15.

17. A mixture of about 70 to 90 parts by weight of a compound of formula (I)

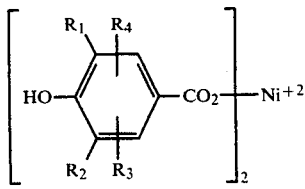

(I)

wherein $R_1$ and $R_2$ are each alkyl radicals having up to 8 carbon atoms at least one of which is branched on the alpha carbon, and $R_3$ and $R_4$ are each hydrogen or an alkyl radical having up to 18 carbon atoms, and about 30 to 10 parts by weight of an ester of an aliphatic or aromatic carboxylic acid, which ester has a boiling point of at least about 250° C.

18. A mixture of claim 17 wherein the compound of formula I is nickel 3,5-di-t-butyl-4-hydroxybenzoate.

19. A mixture of claim 17 or 18 wherein the ester is di-butyl phthalate.

20. A mixture of claim 17 or 18 wherein the ester is n-hexadecyl 3,5-di-t-butyl-4-hydroxybenzoate.

* * * * *